United States Patent [19]
Kert et al.

[11] Patent Number: 5,797,682
[45] Date of Patent: Aug. 25, 1998

[54] DEVICE AND METHOD FOR MEASURING TEMPERTURE OF VEHICLE EXHAUST

[75] Inventors: John Kert, Pismo Beach, Calif.; Robert Stephens, Sterling Heights, Mich.; Michael D. Jack, Goleta, Calif.

[73] Assignee: Envirotest Systems Corp., Sunnyvale, Calif.

[21] Appl. No.: 797,669

[22] Filed: Jan. 31, 1997

Related U.S. Application Data

[63] Continuation of Ser. No. 364,438, Dec. 27, 1994, abandoned, which is a continuation-in-part of Ser. No. 15,730, Feb. 10, 1993, abandoned.

[51] Int. Cl.$^6$ .................. G01J 5/06; G01N 21/25
[52] U.S. Cl. .................. 374/123; 374/127; 374/142; 250/338.5; 250/339.13
[58] Field of Search .................. 374/121, 123, 374/127, 142; 250/338.5, 339.04, 339.13

[56] References Cited

U.S. PATENT DOCUMENTS

| | | |
|---|---|---|
| 3,696,247 | 10/1972 | McIntosh et al. |
| 4,013,260 | 3/1977 | McClatchie et al. |
| 4,061,918 | 12/1977 | Preier et al. |
| 5,418,366 | 5/1995 | Rubin et al. ............ 250/338.5 |
| 5,489,777 | 2/1996 | Stedman et al. ............ 250/338.5 |
| 5,591,975 | 1/1997 | Jack et al. ............ 250/338.5 |

OTHER PUBLICATIONS

Smith et al "Spectroscopic Method for Simulaneous Determination of Species Concentration and Temperature in a Cyclic Composition Process", *The Review of Scientific Instruments.*, vol. 40 No. 12 (Dec. 1969) pp. 1541–1544.

*Primary Examiner*—Diego F.F. Gutierrez
*Assistant Examiner*—Willie Morris Worth
*Attorney, Agent, or Firm*—Hunton & Williams

[57] ABSTRACT

A system (10) for simultaneously measuring temperature and CO, $CO_2$ and HC gas content of vehicle (11) exhaust detects and analyzes a beam of infrared electromagnetic radiation (21) projected through a plume (13) of vehicle exhaust to assess the concentration of CO, $CO_2$, and HC in the vehicle exhaust and detects and analyzes infrared electromagnetic radiation (15) emitted by the plume (13) to assess the temperature of the plume (13) and, consequently, whether the vehicle's (11) catalytic converter is operating in the cold or hot mode. Essentially simultaneous measurement is taken by intermittently interrupting the beam (21) of projected infrared electromagnetic radiation and detecting and analyzing the emitted infrared radiation (15) during the intervals of interruption when the beam (21) is not projected through the plume (13). Intermittent projection of the beam (21) is accomplished by insertion of a chopper wheel (22) between an infrared beam projector (20) and the plume (13).

15 Claims, 5 Drawing Sheets

Fig_3

DEVICE AND METHOD FOR MEASURING TEMPERTURE OF VEHICLE EXHAUST

CROSS-REFERENCE TO A RELATED PATENT APPLICATION

This is a continuation application of Ser. No. 08/364,438 filed 27 Dec. 1994 (now abandoned) that is a continuation-in-part application of Ser. No. 08/015,730 filed 10 Feb. 1993 (now abandoned).

TECHNICAL FIELD OF THE INVENTION

The present invention relates to methods for monitoring exhausts of motor vehicles, and more particularly to a device and method for remotely assessing the temperature of a motor vehicle's tailpipe exhaust as a means for determining whether the vehicle's catalytic converter is in a cold or hot mode of operation.

BACKGROUND OF THE INVENTION

Exhaust from motor vehicles may be monitored to determine the gaseous chemical content thereof. Vehicles which emit greater than desirable amounts of pollutants may be identified through monitoring of vehicle exhausts. High concentrations of pollutants in a vehicle is exhaust is generally attributed to faulty combustion in the engine or a faulty catalytic converter. A catalytic converter plays a major role in reducing air-polluting emissions from a vehicles's exhaust system. The catalytic converter employs a chemical catalyst that reduces polluting emissions by providing for more complete combustion.

A known method of monitoring vehicle exhausts involves detecting and analyzing the concentration of CO, $CO_2$, and HC gases present in an exhaust plume. This monitoring method uses principles of gas spectroscopy to detect concentrations of gases. However, this known method does not determine whether the concentrations of gases detected are from a relatively cold vehicle exhaust plume or from a hot vehicle exhaust plume. The significance of a cold versus hot plume is that a cold exhaust plume would be present when a motor vehicle is in a so-called "cold-start" condition wherein the engine has not run for a period of time sufficient to "warm-up." In the cold-start condition, the monitored vehicle's engine is not running under optimum conditions and the vehicle's emission control elements, such as a catalytic converter, are not yet functioning optimally. For example, if a motor vehicle's catalytic converter is cold (that is, not warmed by running of the engine for a period of time) high concentrations of CO and HC are normally present in the exhaust. Pollutant concentration should be measuring when the catalytic converter is "warm" or "hot", that is, when the engine of the vehicle has run for a period of time to "warm-up." When the engine has warmed, it and the catalytic converter are then generally operating under optimum conditions. In a cold-start condition, an exhaust plume of a vehicle is likely to contain higher concentrations of pollutants then would be present when the exhaust plume is "warm" or "hot". The detection of high concentrations of CO, $CO_2$, and HC gases during cold-start conditions may be misleading if it is not known whether the vehicle is in a cold-start or warm/hot condition.

There is often a need to monitor vehicle exhausts from a point of observation that is remote from the vehicle. For example, governmental agencies charged with monitoring vehicle emissions, so as to reduce air pollution, can monitor a greater number of vehicles if it is not necessary to physically contact each vehicle to determine the exhaust concentration of CO, $CO_2$, and HC and the exhaust temperature. A method for remotely monitoring the temperature or pollutant concentration and temperature of vehicle exhaust emissions is not presently known. Likewise, a method for remotely monitoring the temperature of a vehicle's exhaust emissions as a means for determining the operability of the vehicle's catalytic converter is not presently known.

It is known that gaseous substances such as CO, $CO_2$, and HC characteristically absorb certain frequencies of infrared electromagnetic radiation passing through the gas. The frequencies of electromagnetic radiation absorbed are known as the absorption spectrum for a particular gas. It is also known that a gaseous substance such as CO, $CO_2$, or HC will emit characteristic frequencies of infrared electromagnetic radiation when the gases are excited by the application of heat energy. The frequencies of electromagnetic radiation emitted by hot gases is known as the emission spectrum for each particular gas. There are no known methods for incorporating both the absorption and emission spectra to determine both pollutant content and temperature of vehicle exhausts, or the operability condition (cold-hot) of the vehicle's catalytic converter.

SUMMARY OF THE INVENTION

It is an object of the invention to provide a means for remotely determining whether a vehicle's catalytic converter is operating in a cold or hot mode.

It is a further object of the invention to provide a means for remotely assessing the temperature of a vehicle's exhaust emissions to determine whether the vehicle's catalytic converter is operating in a cold or hot mode.

it is also an object of the invention to provide a means for remotely simultaneously measuring the temperature of an exhaust plume from a moving vehicle along with the ratios of CO to $CO_2$ and HC to $CO_2$ for the plume.

According to a preferred embodiment of the invention, infrared electromagnetic radiation emitted by a vehicle's exhaust emissions is observed to determine the temperature thereof and, consequently, whether the vehicle's catalytic converter is operating in a cold or hot condition. The temperature and pollutant content of exhaust emissions are measured essentially simultaneously by detecting, respectively, infrared electromagnetic radiation "emitted" by exhaust emissions and infrared electromagnetic radiation "projected" through the exhaust. Temperature is determined by detecting emitted infrared electromagnetic radiation of wavelengths corresponding to the emission spectrum of gas found in vehicle exhausts. Pollutant content is determined by detecting projected infrared electromagnetic radiation corresponding to the absorption spectra of CO, $CO_2$, and HC, respectively. In accordance with a preferred embodiment of the invention, infrared electromagnetic radiation is projected through a plume of vehicle exhaust, filtered, and subsequently received by detectors that determine the concentration of CO, $CO_2$, and HC. The projected infrared electromagnetic radiation is only intermittently projected through the plume. During intervals of non-projection, when the electromagnetic radiation is not projected through the exhaust plume, the filtering and detecting components are able to receive and analyze infrared electromagnetic radiation emitted by the exhaust gases. Concentrations of CO, $CO_2$, and HC are measured during intervals when infrared electromagnetic radiation is projected through the exhaust plume. Temperature of the exhaust is measured during intervals of non-projection.

In accordance with a system and method for measuring a temperature of a vehicle exhaust that contains chemical species of interest, the following steps are executed: (a) intermittently projecting a beam of IR radiation through a region; and (b) prior to the passage of a vehicle through the region, obtaining a first measurement of an absorption of the beam within the region, during a time that the beam is projected, and obtaining a second measurement of an emission of IR radiation from within the region, during a time that the beam is not projected. Further steps of the method include, after the passage of a vehicle through the region, (c) obtaining a third measurement, during a time that the beam is projected, of an absorption of the beam within the vehicle's exhaust by at least one chemical species of interest, and (d) obtaining a fourth measurement, during a time that the beam is not projected, of an emission of IR radiation from within the vehicle's exhaust by the least one chemical species of interest. Next, the method (e) determines a concentration of the at least one chemical species of interest in accordance with the first and third measurements, and then (f) determines a temperature of the vehicle's exhaust in accordance with the determined concentration and in accordance with the second and fourth measurements.

Other aspects, objects, features, and advantages of the present invention will become apparent to those skilled in the art upon reading the detailed description of preferred embodiments.

DETAILED DESCRIPTION OF PREFERRED EMBODIMENTS

While the specification concludes with claims particularly pointing out and distinctly claiming the subject matter which is regarded as the present invention, the invention will now be described with reference to the following description of embodiments taken in conjunction with the accompanying drawings. Throughout the drawings the same numerals are used to refer to like features.

As an overview, the invention uses the characteristics of the absorption and emission spectra of CO, $CO_2$, and HC gases contained in the exhaust of a motor vehicle to determine the concentration of those air-pollutants in the exhaust and to assess the temperature of the exhaust. CO, $CO_2$, and HC content of vehicle exhaust are measured by detecting the quantity of wavelengths of infrared electromagnetic radiation which are characteristically absorbed from electromagnetic radiation by CO, $CO_2$, and HC gases. Detection of smaller, or decreased, quantities of the characteristics wavelengths indicates greater absorption by the exhaust and, therefore, the presence of greater amounts of CO, $CO_2$, and HC, and, thus, a catalytic converter or engine which is not optimally performing. Greater quantities of characteristic wavelengths indicate the presence of smaller amounts of CO, $CO_2$, and HC gas, and thus, a properly-functioning catalytic converter and engine. Temperature of exhaust is measured by detecting the quantity of wavelengths of infrared electromagnetic radiation which are characteristically emitted by CO, $CO_2$, or HC gas at a predetermined temperature. Detection of smaller, or decreased, quantities of characteristic hot-exhaust gas wavelengths indicates a lower exhaust temperature, and thus, a catalytic converter which is cold. Greater quantities of characteristic hot-exhaust gas wavelengths indicate higher exhaust temperatures, and thus a catalytic converter which is hot. The concentration of CO, $CO_2$, and HC gases and the ratios of $CO-CO_2$ and $HC-CO_2$ together with the temperature of the exhaust provide a good indicator of whether the vehicle is operating within desirable pollution control parameters. The invention allows these measurements to be taken from a vantage point which is remote with respect to a moving vehicle.

Figure 1:
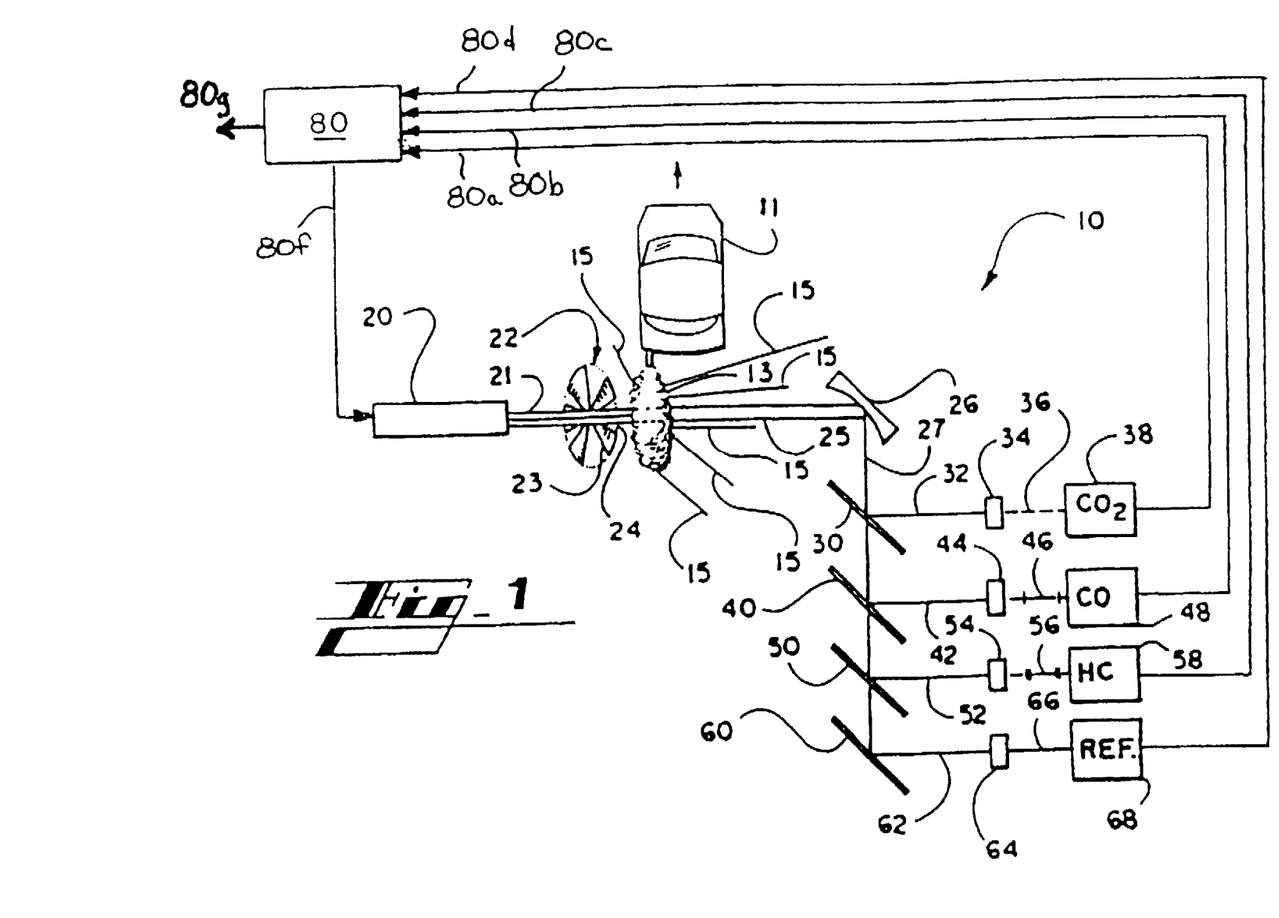
FIG. 1 is a schematic illustration of a system for remote measurement of temperature and air-pollutant content of vehicle exhaust according to a preferred embodiment of the invention.

Referring first to FIG. 1, therein is illustrated a system 10 for remote measurement of temperature and air-pollutant content of vehicle exhaust. The system 10 takes measurements of exhaust from a moving vehicle 11. The system 10 measures the pollutant content of a plume 13 of vehicle exhaust by projecting a beam of infrared electromagnetic radiation through the plume and then analyzing the exiting beam to determine the intensity of wavelengths of electromagnetic radiation that would be absorbed by CO, $CO_2$, and HC gases. An infrared radiation projector 20 projects a beam of infrared electromagnetic radiation 21 through the plume 13. The beam 21 consists of wavelengths of infrared electromagnetic radiation that will include the wavelengths of electromagnetic radiation that would be characteristically absorbed by CO, $CO_2$, and HC pollutants. The system's 10 detection components receive projected radiation which has had certain frequencies absorbed by gases in the exhaust plume 13. The system 10 essentially simultaneously measures the temperature of the exhaust plume 13. The heat energy present in gases such as CO, $CO_2$, and HC causes the gases to emit characteristic wavelengths of electromagnetic radiation. The system 10 measures the temperatures of the exhaust plume 13 by sensing characteristic wavelengths of infrared electromagnetic radiation emitted by at least one of the gases found in the exhaust plume 13. The same detection components of the system 10 act as emission spectra sensors for emitted infrared electromagnetic radiation 15 when the infrared beam 21 is interrupted. Infrared electromagnetic radiation 15 is continuously emitted by the gases of the exhaust plume 13. When the projected beam 21 is interrupted, only the emitted infrared electromagnetic radiation 15 is seen by the detecting components of the system 10. Periodic interruption of the projected beam 21 is accomplished by use of a chopper wheel 22 which has alternating radiation impervious 23 and radiation transparent 24 sections. As the wheel 22 rotates, the beam of infrared electromagnetic radiation 21 is intermittently projected through the exhaust plume 13. During an interval of beam 21 projection through the plume 13, CO, $CO_2$, and HC gases in the plume 13 absorb electromagnetic radiation from the beam 21. The intensity of electromagnetic radiation of wavelengths characteristically absorbed by CO, $CO_2$, and HC gases will be diminished in the exiting beam 25. The exiting beam 25 is directed to sensors adapted for detecting the intensity of electromagnetic radiation of characteristically absorbed wavelengths.

The system 10 illustrated in FIG. 1 uses a beam splitter arrangement to direct the beam 25 to multiple detectors. A mirror 26 reflects reflected beam 27 to multiple beam splitters 30, 40, 50 and mirror 60. In the system 10 illustrated, four detection components are used. Three are used to detect concentrations of the respective CO, $CO_2$, and HC gases while the fourth is used as a reference reading to normalize the other readings. In this regard the output of the reference channel (60, 62, 64, 68) is used to divide into the other obtained readings, thereby compensating for road dust and other IR obscurations that effect all of the measurement channels. Each beam splitter 30, 40, 50 and the mirror 60 direct an identical image of the beam 27 to distinct detectors. Each detection component is spectrally selective and utilizes a filter to filter out those wavelengths (frequencies) of infrared electromagnetic radiation that would not be characteristically absorbed by one of the gases. In the detection components of FIG. 1, the first beam splitter 30 directs the beam 32 through a filter 34 which filters out wavelengths of electromagnetic radiation not characteristically absorbed by $CO_2$ gas. The filtered beam 36 is then received by the $CO_2$ detector 38 which measures the intensities of characteristically absorbed wavelengths of infrared electromagnetic energy. Likewise beam splitter 40 directs beam 42 through filter 44. The filtered beam 46 is received by the CO detector 48. As before, the filter 44 filters out all but those wavelengths of electromagnetic radiation characteristically absorbed by CO. Beam splitter 50 directs beam 52 through filter 54. The filtered beam 56 is received by the HC detector 58. The mirror 60 directs beam 62 through the filter 64 of the reference segment of the detection components. The filtered beam 66 is received by the reference detector 68. The filter 64 filters out frequencies of infrared electromagnetic radiation that are not necessary for comparison of the intensities of wavelengths of electromagnetic radiation detected by the $CO_2$ 38, CO 48, and HC 58 detectors.

Figure 2:
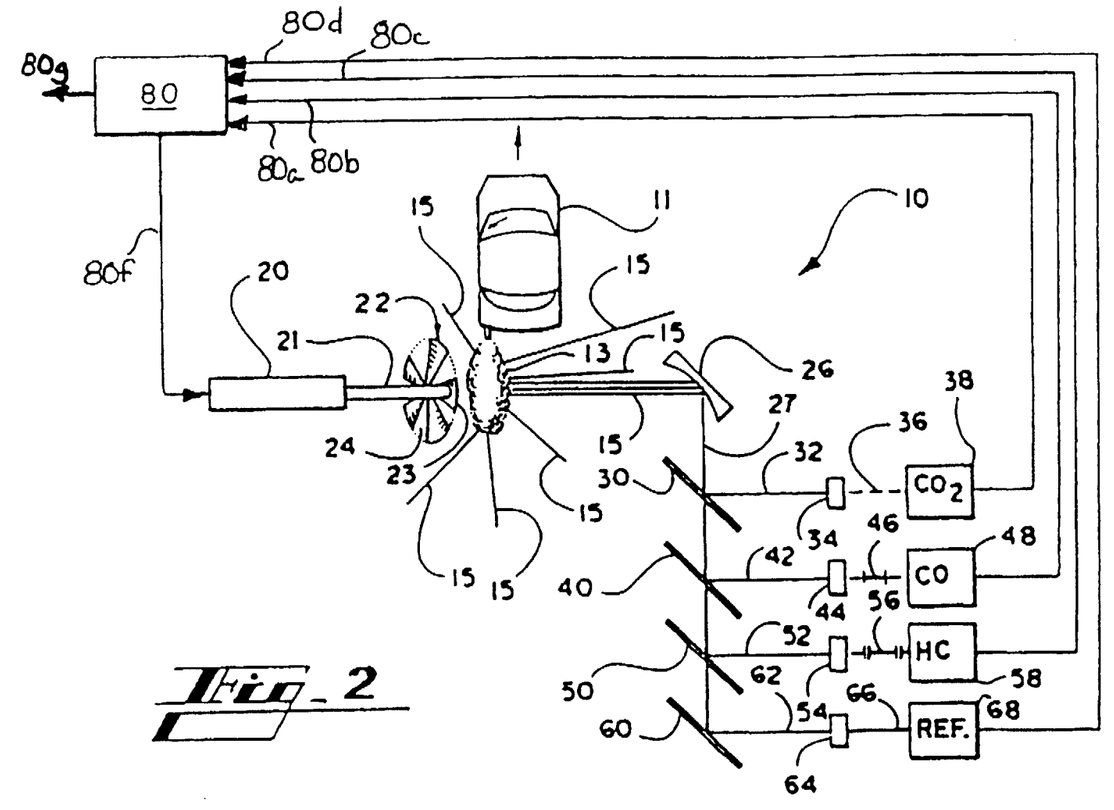
FIG. 2 illustrates the invention of FIG. 1 with the chopper wheel rotated to a position preventing projection of infrared electromagnetic radiation.

Referring now to FIG. 2, the components of the system 10 remain the same. The electromagnetic radiation 15 emitted by the plume 13 is read during an interval of intermittency when a radiation-impervious section 23 of the chopper wheel 22 has been rotated to interrupt the projection of the beam 21. The chopper wheel 22 may revolve at fairly high rates of speed. A rate of 200 revolutions per second is suitable. Although emission spectra for several gases may be analyzed, it is possible to utilize the emission spectra of only one gas to determine the temperature of the exhaust plume 13. For example, the emission spectrum for $CO_2$ may be used to determine exhaust temperature. As illustrated in FIG. 2, when the beam 21 is no longer projected, only emitted electromagnetic radiation 15 is directed to the mirror 26 and reflected as beam 27 to the beam splitters. A more precise measurement of exhaust plume 13 temperature may be taken by a more precise reading of the intensity of emitted radiation. A more precise intensity reading may be taken by causing the detector to receive periodic projections of emitted radiation in a manner similar to the calculation of the area under a curve in calculus by dividing that area into small increments.

Figure 3:
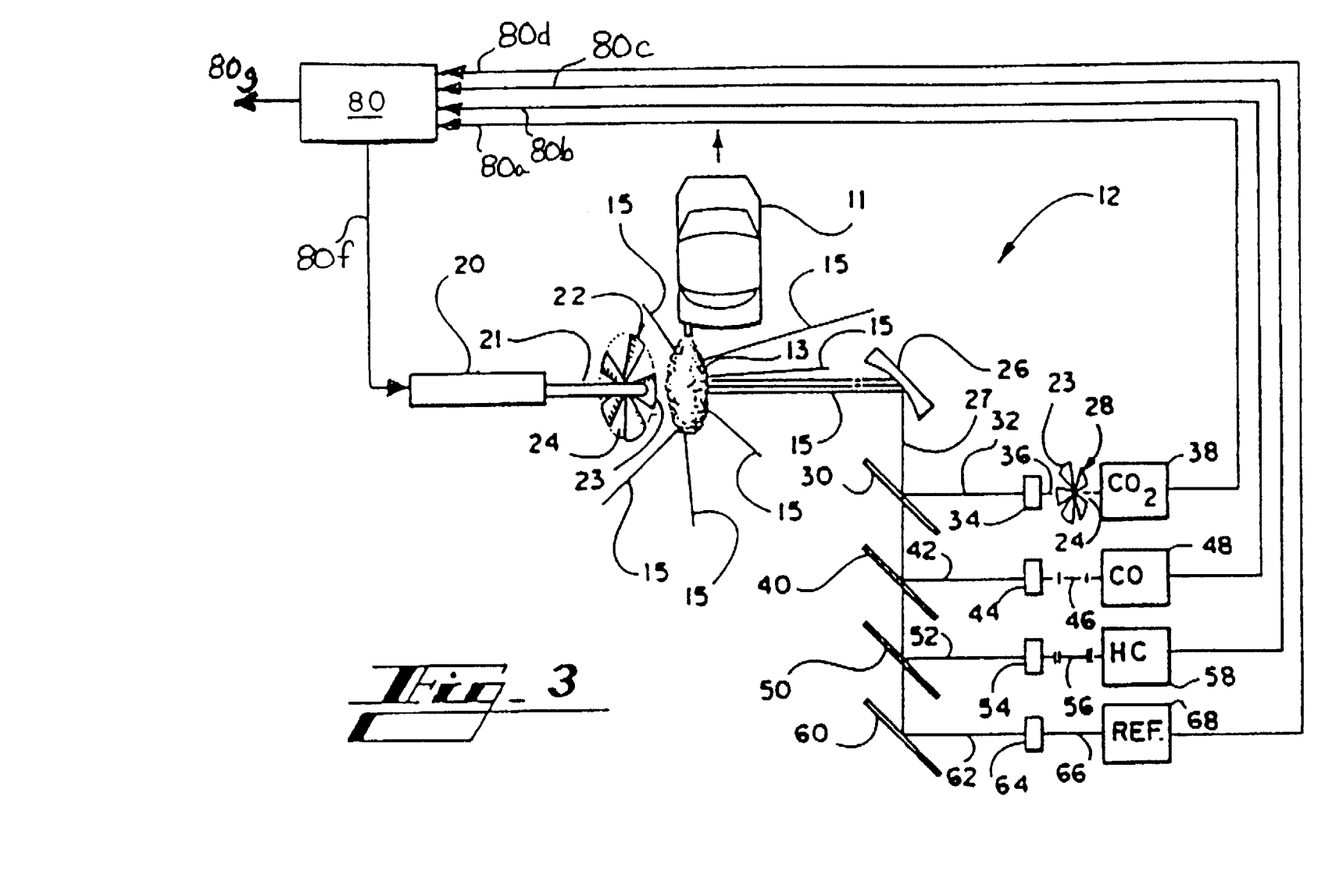
FIG. 3 is another schematic illustration of the invention of FIG. 1 with an additional chopper wheel.

Referring now to FIG. 3, a system 12 identical to the previously discussed system 10 contains a second chopper wheel 28 which allows the detector 38 to analyze shorter intervals of radiation. An additional chopper wheel 28, like the first chopper wheel 22, has alternating radiation impervious 23 and radiation transparent 24 sections. This addition, or second, chopper wheel 28 revolves faster than the first chopper wheel 22 so that multiple readings may be taken during one blocking interval of the first chopper wheel. A revolution rate of at least 10 times the rate of the first chopper wheel 22 is suitable for the additional chopper wheel 28.

Figure 4:
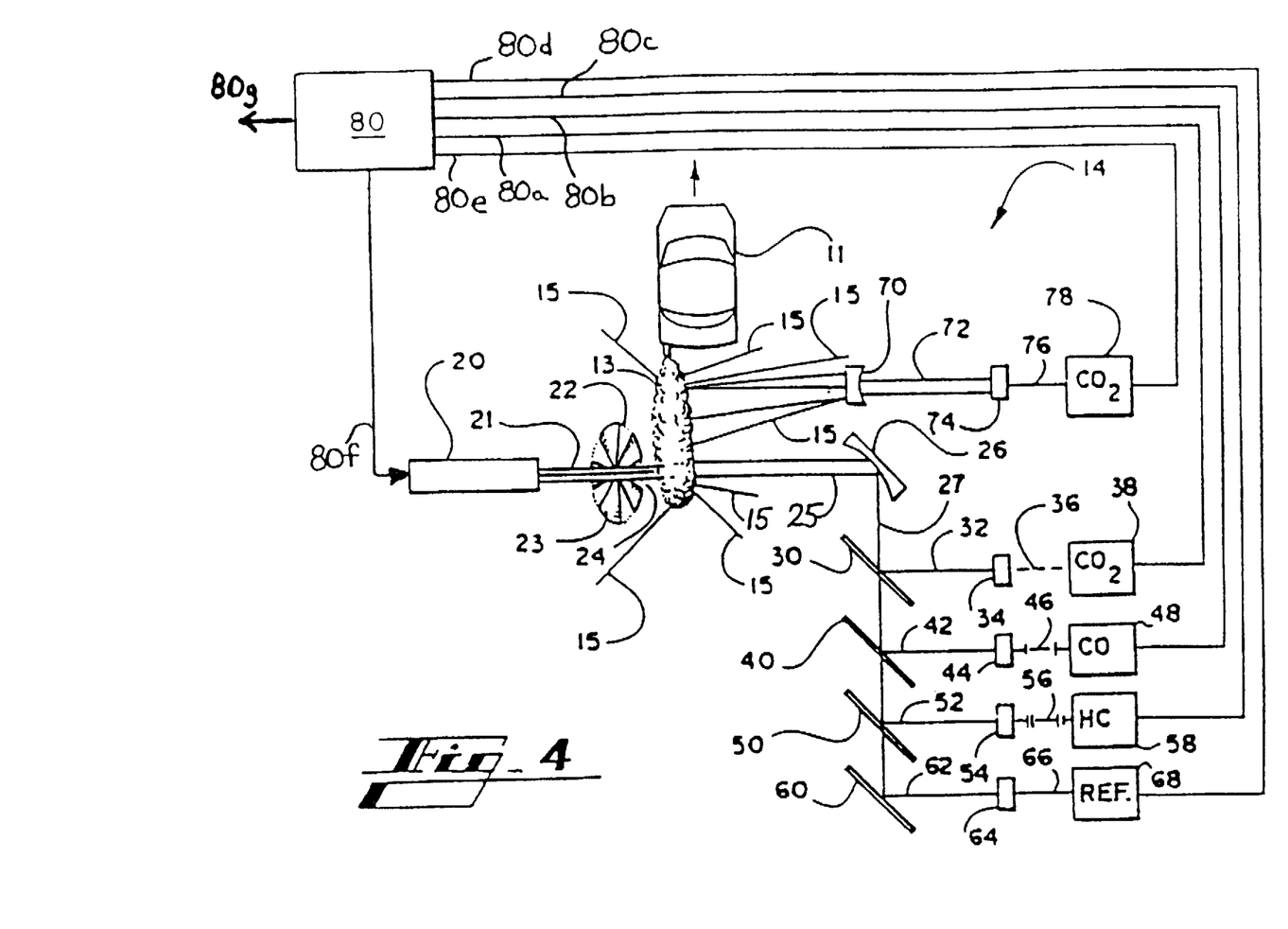
FIG. 4 is a schematic illustration of a system for remote measurement of temperature and air-pollutant content of vehicle exhaust according to another preferred embodiment of the invention.

The systems 10, 12 shown in FIGS. 1, 2, and 3 utilize a single detection network to analyze both projected beam 21 and emitted radiation 15. However, it is also possible to utilize distinct detection components for each radiation source. Referring now to FIG. 4, therein is shown a system for remotely measuring temperature and air-pollutant content of vehicle exhaust 14 according to another preferred embodiment of the invention. The system 14 contains all of the elements previously described but has an additional detecting component distinct from the detection components previously described. In general, the detection component for emitted radiation 15 also contains a filter 74 and $CO_2$ detector 78. These elements may be preceded by a collimator 70 for projecting randomly disbursed emitted radiation as a beam 72 to be passed through the filter 74.

In operation, the system 10, 12, 14 is installed at a point along a thoroughfare or other location traveled by motor vehicles. The infrared projector 20 and chopper wheel 22 are placed on one side of the thoroughfare opposite the beam splitting and detection components. One or more conventional photo-interrupter circuits (not shown) can be used to detect the approach and/or presence of a vehicle within the detection zone or region through which the beam 21 passes. A reading of existing, or residual background, radiation in the area is taken prior to the vehicle's 11 passage of the detection point. This reading serves as a reference emission reading, and is taken during the time that the beam of infrared radiation 21 is blocked. As the vehicle 11 passes the projector 20, the beam of infrared radiation 21 is projected through the exhaust plume 13. The beam 25 exiting the plume 13 and electromagnetic radiation emitted 15 by the plume 13 are directed to the detecting components of the various embodiments of the system 10, 12, 14 and are analyzed, preferably, by a data processor 80 as described in greater detail below.

Although the data gathered by the system 10 may be analyzed manually; preferably, the data is analyzed with the processor 80 to determine whether a monitored vehicle 11 is operating within acceptable pollution parameters. The system 10 is able to detect high concentrations of CO and HC pollutants, and additionally assesses whether the plume 13 is cold or hot. If the plume 13 is determined to be cold, high concentrations of pollutants may be regarded as unreliable data. If the plume 13 is determined to be hot, high concentrations of pollutants may be relied upon to assess the vehicle's 13 conformance to pollution control standards.

Having described the overall operation of the systems 10, 12 and 14 of FIGS. 1–4, various signal processing operations that are executed by the processor 80 will now be described in further detail.

The processor 80 receives inputs (80a–80e) from the detectors 38, 48, 58, 68 and 78 of FIGS. 1–4, and has an output 80f coupled to the infrared radiation projector 20 for controlling the operation thereof. By example, the projector 20 may be a blackbody source. The processor 80 will generally include amplifiers (not shown) and at least one analog-to-digital converter (not shown) for converting the detector outputs to corresponding digital values. The use of such circuits in conjunction with detectors of IR radiation, such as photodetectors and pyrometers, is well known in the art. The processor 80 also has an output 80g for outputting the results of the computations done on the signals present on the input lines 80a–80e.

The $CO_2$ filter 34 may have a passband centered 4.2 micrometers, the CO filter 44 a passband centered on 4.6 micrometers, the HC filter a passband centered on 3.3 micrometers, and the reference channel filter 64 may have a passband centered on 3.8 micrometers (a wavelength not strongly absorbed or emitted by any of the chemical species of interest in the exhaust plume 13). As was indicated above, the output of the reference detector 68 is used to normalize the other detectors to compensate for optical impairments that are common to all of the chemical species measurement channels. The $CO_2$ emission channel filter 74 of FIG. 4 may also have a passband centered on 4.2 micrometers, or another wavelength that is associated with a $CO_2$ emission line may be used.

In general, the temperature of the exhaust plume 13 is determined by measuring the radiant power of the exhaust plume using detectors 38, 48, 58 and 68. To accurately accomplish this function the radiant power of the exhaust plume 13 must be distinguishable from all other sources of radiant power. This is preferably accomplished by measuring the radiant power with detectors 38, 48, 58 and 68 with: (a) the absence of an exhaust plume and the chopper closed (IR beam 21 blocked) ; (b) the absence of an exhaust plume and the chopper open; (c) the presence of an exhaust plume and the chopper closed; and (d) the presence of an exhaust plume and the chopper open. The difference in detector signal measured by the processor 80 during case (c) and case (a) (i.e., when the IR beam 21 is blocked by the chopper 22) is a function of the radiant power of the exhaust plume 13. The radiant power of the exhaust plume 13 is a function of both the temperature and the concentration of the radiating chemical species in the plume 13. The difference in detector signal measured during case (d) and case (b) (i.e., when the IR beam 21 is passed through the chopper 22) is a function of the concentration of the chemical species of interest in the plume 13. Hence, by measuring the concentration of the chemical species in the exhaust plume, and by measuring the radiant power of the exhaust plume, the temperature of the exhaust plume can be ascertained.

Figure 5:
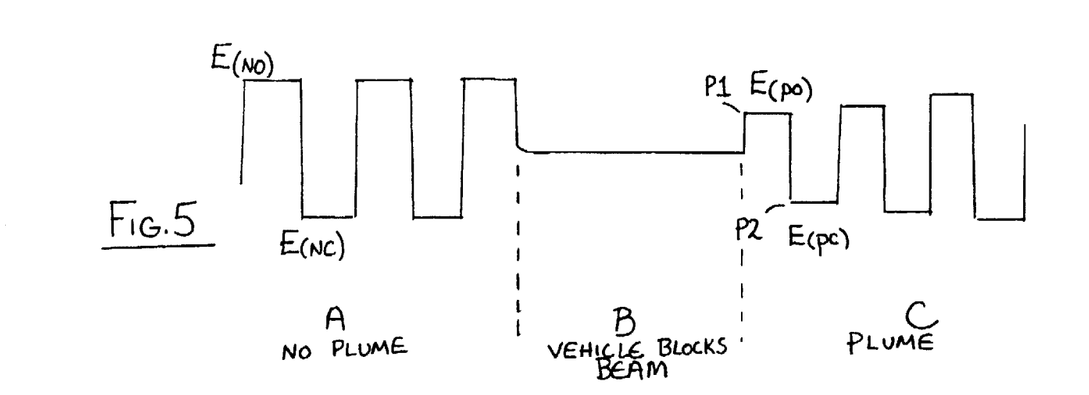
FIG. 5 illustrates a trace of voltage versus time, which is typical of the signals from the detectors 38, 48, 58 and 68 of FIGS. 1–4.

FIG. 5 illustrates a trace of voltage versus time, which is typical of the signals output from the detectors 38, 48 and 58. FIG. 5 depicts detector voltage outputs without an exhaust plume present (region A), during the time that a passing vehicle blocks the beam 21 (region B), and after the passage of the vehicle and in the presence of the exhaust plume 13 (region C). The reduced amplitude at point P1 is due to absorption of the beam 21 within the exhaust plume 13, while the increased amplitude at point P2 (relative to the detector voltage measured in region A) is due to emission from the plume 13, as will now be described in detail.

The detector voltages ($E_d$) are proportional to the radiant power ($P_\upsilon$) present at the detector:

$$E_d = \alpha P_\upsilon + a \quad (1)$$

where $\alpha$ is a proportionality constant expressed in Volta per Watt, and 'a' is the detector voltage in the absence of any radiant power present at the detector. Values of $\alpha$ and 'a' can be experimentally determined for known levels of radiant power.

The radiant power at the detector $P(nc)_\upsilon$, when no exhaust plume 13 is present and the chopper 22 is closed, is equal to:

$$P(nc)_\upsilon = (A_m A_g/L(a)2)N(bkg)_\upsilon(t)e^{-\kappa(a)L(a)} \quad (2)$$

where $\kappa(\alpha)$ is the absorption coefficient for the atmosphere (a) at wavelength $\upsilon$ for any molecular species that absorbs wavelength $\upsilon$ present between infrared source 20 and detectors 38, 48, 58 and 68. L(a) is the distance between any radiant objects that are viewed by the detector and the detectors, $A_m$ is the area of the collection optic (e.g. mirror, lens, or iris) of the detector, $A_g$ is the area occupied by the radiant objects (as observed by the detector), and $N(bkg)\upsilon(t)$ is the power radiated per unit solid angle by the radiant objects at some temperature (t) that are within the viewing angle of the detector. Hence, $P(nc)_\upsilon$ is a function of the solid angle observed by the detector and the radiant power, $N(bkg)_\upsilon(t)$ of all objects viewed by the detector, where t is the temperature of the objects, and L is the distance between the objects and the detectors. The units of N are Watts $cm^{-2}$.

The detector 38, 48, 58 and 68 voltages, $E(no)_d$ (proportional to $P(no)_\upsilon$) and $E(nc)_d$ (proportional to $P(nc)_\upsilon$), are measured prior to a vehicle 11 entering the infrared beam 21, i.e. when no exhaust plume 13 is present (region A of FIG. 5). The detector 38, 48, 58 and 68 voltages, $E(po)_d$ (proportional to $P(po)_\upsilon$) and $E(pc)_d$ (proportional to $P(pc)_\upsilon$), are also measured after a vehicle 11 exits the infrared beam 21, i.e., when an exhaust plume 13 is present (region C of FIG. 5).

During the time that the chopper 22 is open and no exhaust plume 13 is present the radiant power at the detector, $P(no)_\upsilon$ is:

$$P(no)_\upsilon = (A_m A_g/L^2)N(s)_\upsilon(t)e^{-\kappa(a)L(a)} + P(nc)_\upsilon \quad (3)$$

where $N(s)_\upsilon(t)$ is the radiant power of the infrared source 20. Hence, when no exhaust plume 13 is present, the difference between the detector voltage when the chopper 22 is open, $E(no)_d$, and the detector voltage when the chopper 22 is closed, $E(nc)_d$, is:

$$E(no)_d - E(nc)_d = \alpha P(no)_\upsilon - \alpha P(nc)_\upsilon = \alpha(P(no)_\upsilon - P(nc)_\upsilon) \quad (4)$$

In the presence of an exhaust plume 13, and when the chopper 22 is closed, the radiant power $P(pc)_\upsilon$, at the detector is:

$$P(pc)_\upsilon = (1-e^{-\kappa(p)L(p)})(A_m A_g/L^2)N(p)_\upsilon(t)e^{-\kappa(a)L(a)} + P(nc)_\upsilon \quad (5)$$

where $N(p)_\upsilon(t)$ is the radiant power of the exhaust plume 13 at temperature t, and $\kappa(p)$ is the absorption coefficient of the plume, L(p) is the distance through the exhaust plume 13 that the radiant power from the exhaust plume is transmitted. The relationship between $N(p)_\upsilon$ and t can be predetermined.

In the presence of an exhaust plume 13, and when the chopper 22 is open, the radiant power $P(po)_\upsilon$, at the detector is:

$$P(po)_\upsilon = (1-e^{-\kappa(p)L(p)})(A_m A_g/L^2)N(s)_\upsilon(t)e^{-\kappa(a)L(a)} + P(no)_\upsilon \quad (6)$$

Hence, when an exhaust plume 13 is present, the difference in detector voltage when the chopper is open, $E(po)_d$, and the detector voltage when the chopper is closed, $E(pc)_d$, is given by:

$$E_d(po) - E_d(pc) = \alpha P(po)_\upsilon - \alpha P(pc)_\upsilon = \alpha(P(po)_\upsilon - P(pc)_\upsilon) \quad (7)$$

The value of $\kappa$ can be experimentally predetermined and stored in a memory of the processor 80, for all chemical species present in a vehicle exhaust plume 13 that absorb wavelength $\upsilon$, by determining the following relationship at several values of C:

$$\kappa = (E_d(po) - E_d(pc))/CL \quad (8)$$

where C is the concentration of any molecular species that absorbs wavelength $\upsilon$ present in a known pathlength L. Hence, in the presence of the vehicle exhaust plume 13 the value of CL is determined by measuring $E(po)_d - E(pc)_d$.

The radiant power of the exhaust plume 13 $N(p)_\upsilon$ can be determined by measuring $E(po)_\upsilon - E(nc)_\upsilon$. It is thus clear that by knowing CL and N(p) the temperature (t) of the exhaust plume 13 can be determined, which is the desired result. Having determined the temperature of the exhaust plume 13 and, thus, an indication of the temperature of the vehicle's catalytic converter, the processor 80 is enabled to determine whether the determined concentrations of chemical species of interest are valid. That is, and if the catalytic converter is determined to have reached a suitable operating temperature, an excessively high concentration of one or more of the chemical species of interest may indicate a vehicle that is exceeding mandated maximum emission levels. Conversely, if the catalytic converter is still "cold" the measured concentrations of the chemical species of interest may not be an accurate indication of the performance of the vehicle's emission control system(s).

In greater detail, the temperature of the exhaust gases as they leave the tailpipe can be determined as follows. By example, if only the 4.4 micrometer emission band of carbon dioxide shown in FIG. 6 is considered, the radiance can be found by an integration:

$$N = \frac{0.5}{\pi} \int_{4\mu}^{5\mu} \epsilon(\lambda) W_\lambda d\lambda, \quad (9)$$

where $\epsilon(\lambda)$ is the spectral emissivity of the exhaust plume gases and $W_\lambda$ is the spectral radiant emittance of a blackbody.

Figure 6:
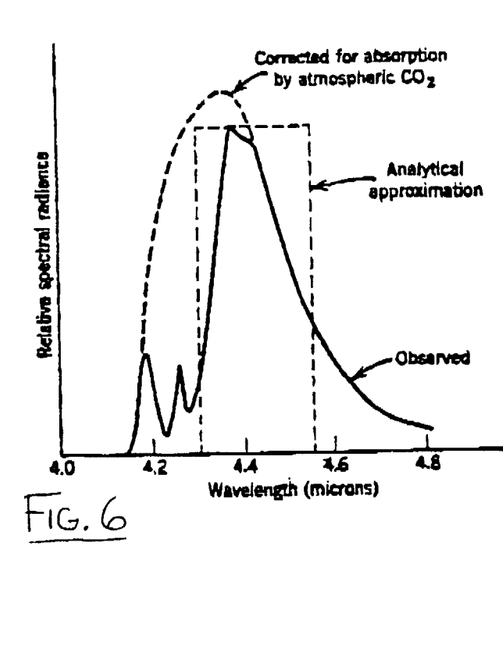
FIG. 6 is a graph depicting relative spectral radiance versus wavelength for $CO_2$.

Evaluation of the integral of Eq. 9 can be simplified by the assumption that the emission bands can be approximated by the dotted rectangular curve shown in FIG. 6. In effect, this procedure assigns a constant value to $\epsilon(\lambda)$, assumed here to be 0.5, between 4.3 micrometers and 4.55 micrometers, and a value of zero outside this interval.

With this change, the integral becomes $$N = \frac{0.5}{\pi} \int_{4.3\mu}^{4.55\mu} W_\lambda d\lambda. \quad (10)$$

The value of the integral, $3.49 \times 10^{-2}$ W cm$^{-2}$, is calculated from Eq. 11.

Planck's law describes the spectral distribution of the radiation from a blackbody as:

$$W_\lambda = \frac{2\pi hc^2}{\lambda^5} \frac{1}{e^{ch/\lambda kT} - 1}, \quad (11)$$

which is usually written as $$W_\lambda = \frac{c_1}{\lambda^5} \frac{1}{e^{c_2/\lambda T} - 1}, \quad (12)$$

where $W_\lambda$=spectral radiance emittance, W cm$^{-2}\mu^{-1}$, where W is Watts,
$\lambda$=wavelength, $\mu$,
h=Plank's constant
  =$(6.6256 \pm 0.0005) \times 10^{-34}$ Wsec$^2$,
T=absolute temperature, °K,
c=velocity of light
  =$(2.997925 \pm 0.000003) \times 10^{10}$ cm sec$^{-1}$,
$c_1 = 2\pi hc^2$=first radiation constant
  =$(3.7415 \pm 0.0003) \times 10^4$ Wcm$^{-2}\mu^4$,
$c_2 = ch/k$=second radiation constant
  =$(1.43879 \pm 0.00019) \times 10^4 \mu$°K, and
k=Boltzmann's constant
  =$(1.38054 \pm 0.00018) \times 10^{-22}$ Wsec °K$^{-1}$.

Figure 7:
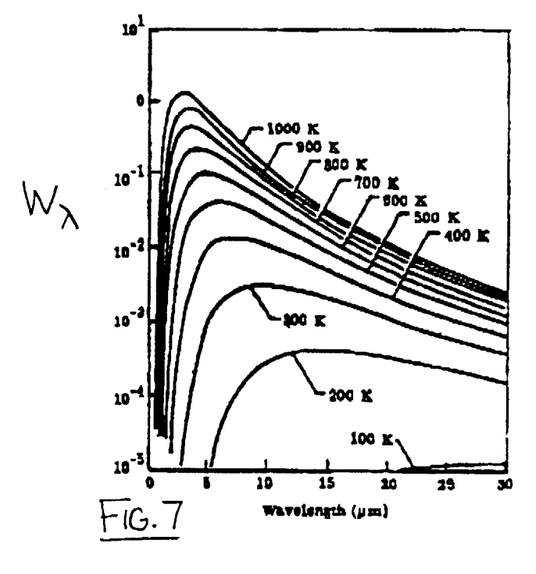
FIG. 7 is a graph that depicts blackbody curves for temperatures in the range of 100° K to 1000° K.

Curves such as those illustrated in FIG. 7 graphically depict the variation of $W_\lambda$ versus $\lambda$ as a function of temperature. These curves show an order of magnitude variation in $W_\lambda$ between ambient temperature (300° K) and a typical exhaust temperature (400° K or 127° C). A total flux density of approximately 1 mW/cm$^2$ is seen at 400° K versus approximately 50 microwatts/cm$^2$ at 300° K. This large variation in flux density enables the processor 80 to determine the temperature of the exhaust plume 13 and, hence, to determine if the vehicle's catalytic converter 11 has reached a suitable operating temperature.

It should be noted that the emission wavelengths that are measured need not correspond to the absorption wavelengths that are measured. In this regard filters can be used that have more than one passband, or variable filters can be used that can be tuned in their passband characteristic. Alternately, the filter passband can be made wide enough to accommodate both emission and absorption lines of interest for a given chemical species of interest.

As should be apparent from the foregoing specification, the invention is susceptible of being modified with various alterations and modifications which may differ from those which have been described in the preceding specification and description. By example, suitable corrections are employed to compensate for any attenuation in the infrared electromagnetic radiation that is due to passage through the beam splitters 30, 40 and 50. Accordingly, the following claims are intended to cover all alterations and modifications which do not depart from the spirit and scope of the invention.

What is claimed is:

1. A system for measuring temperature and CO, $CO_2$ and HC content of a vehicle exhaust comprising:

means for intermittently projecting infrared electromagnetic radiation through a plume of vehicle exhaust; and means for receiving the infrared electromagnetic radiation which has passed through the plume of vehicle exhaust and for receiving infrared electromagnetic radiation emitted by the exhaust plume during intervals when said means for intermittently projecting infrared electromagnetic radiation through a plume of vehicle exhaust does not project infrared electromagnetic radiation through the exhaust plume, means, responsive to the received infrared electromagnetic radiation, for detecting an intensity of predetermined wavelengths of electromagnetic radiation which are characteristics of absorption and emission spectra of CO, $CO_2$ and HC gases; and means for computing the temperature, CO, $CO_2$, and HC content of the plume based on the detected intensities.

2. The invention of claim 1, wherein said computing means comprises:

means for computing the CO, $CO_2$, and HC content of the plume based upon the detected intensity of the predetermined wavelengths of the infrared electromagnetic radiation which has passed through the plume of vehicle exhaust which correspond to the absorption spectra of CO, $CO_2$ and HC, and for computing the temperature of the plume based upon the detected intensity of the predetermined wavelengths of the infrared electromagnetic radiation emitted by the exhaust plume during intervals when said means for intermittently projecting infrared electromagnetic radiation through a plume of vehicle exhaust does not project infrared electromagnetic radiation through the exhaust plume, the detected intensity of the predetermined wavelengths corresponding to the emission spectra of CO, $CO_2$ and HC gases when heated to at least a predetermined temperature.

3. The invention of claim 2, further comprising means for computing a ratio of the content of CO to $CO_2$ and a ratio of the content of HC to $CO_2$.

4. The invention of claim 2, wherein said predetermined temperature comprises a temperature corresponding to a hot catalytic converter of the vehicle.

5. The invention of claim 1, wherein said means for intermittently projecting infrared electromagnetic radiation through a plume of vehicle exhaust comprises an infrared electromagnetic radiation source generating a beam of infrared electromagnetic radiation and a first chopper wheel interposed between said source and said plume of vehicle exhaust for periodically blocking the beam at a first predetermined rate.

6. The invention of claim 5, further comprising a second chopper wheel positioned before said means for detecting an intensity of predetermined wavelengths of electromagnetic radiation, said second chopper wheel being adapted for intermittently allowing and preventing passage of the electromagnetic radiation emitted from the plume of vehicle exhaust at a second predetermined rate that is at least ten times the first predetermined rate of said first chopper wheel.

7. A system for simultaneously measuring temperature and CO, $CO_2$, and HC gas content of vehicle exhaust comprising:

means for projecting a beam of infrared electromagnetic radiation through a plume of vehicle exhaust;

a chopper wheel positioned between said means for projecting a beam of infrared electromagnetic radiation and the plume of vehicle exhaust, said chopper wheel being adapted for intermittently projecting the beam of infrared electromagnetic radiation through the plume of vehicle exhaust;

first means for detecting intensities of wavelengths of infrared electromagnetic radiation characteristically absorbed from the beam of infrared electromagnetic radiation by CO present in the vehicle exhaust;

second means for detecting intensities of wavelengths of infrared electromagnetic radiation characteristically absorbed from the beam of infrared electromagnetic radiation by $CO_2$ present in the vehicle exhaust;

third means for detecting intensities of wavelengths of infrared electromagnetic radiation characteristically absorbed from the beam of infrared electromagnetic radiation by hydrocarbons HC present in the vehicle exhaust;

fourth means for detecting intensities of wavelengths of infrared electromagnetic radiation that are not characteristically absorbed from the beam of infrared electromagnetic radiation by CO, $CO_2$, and HC present in the radiation vehicle exhaust;

beam splitting means for directing the beam of infrared electromagnetic radiation after passing through the plume of vehicle exhaust and infrared electromagnetic radiation emitted by the plume of vehicle exhaust, to said first means for detecting intensities of wavelengths of infrared electromagnetic radiation, said second means for detecting intensities of wavelengths of infrared electromagnetic radiation, said third means for detecting intensities of wavelengths of infrared electromagnetic radiation, and said fourth means for detecting intensities of wavelengths of infrared electromagnetic radiation;

means, responsive to detected intensities of wavelengths of infrared electromagnetic radiation output by said fourth means prior to projection of the beam of infrared electromagnetic radiation through the plume of vehicle exhaust, for determining a reference intensity value for normalizing the detected intensities of wavelengths of infrared electromagnetic radiation output from said first, second and third intensity detecting means; and means for computing the temperature, CO, $CO_2$, and HC content of the plume based at least in part on the normalized detected intensities.

8. The invention of claim 7, wherein said chopper wheel blocks projection of the infrared radiation at a rate of about 200 times per second.

9. The invention of claim 7, wherein said computing means comprises:

means for computing amounts of CO, $CO_2$, and HC in the plume of vehicle exhaust based upon the intensities of wavelengths of infrared electromagnetic radiation detected by said first means for detecting intensities of wavelengths of infrared electromagnetic radiation, said second means for detecting intensities of wavelengths of infrared electromagnetic radiation, and said third means for detecting intensities of wavelengths of infrared electromagnetic radiation, as normalized by the intensities of wavelengths of infrared electromagnetic radiation detected by said fourth means for detecting intensities of infrared electromagnetic radiation; and means for computing the temperature of the plume based upon the detected intensity of the predetermined wavelengths of the infrared electromagnetic radiation emitted by the exhaust plume during intervals when said means for intermittently projecting infrared electromagnetic radiation through a plume of vehicle exhaust does not project infrared electromagnetic radiation through the exhaust plume, said detected intensity of the predetermined wavelengths corresponding to the emission spectra of CO, $CO_2$, and HC gases when heated to at least a predetermined temperature.

10. The invention of claim 9, wherein said predetermined temperature is a temperature corresponding to a hot catalytic converter of the vehicle.

11. The invention of claim 7, and further comprising an additional chopper wheel positioned before at least one of said first means for detecting intensities of infrared electromagnetic radiation, said second means for detecting intensities of infrared electromagnetic radiation, and said third means for detecting intensities of infrared electromagnetic radiation, said additional chopper wheel being adapted for intermittently allowing passage of infrared electromagnetic radiation emitted from the plume of vehicle exhaust at a rate at least 10 times a rate of said chopper wheel.

12. An apparatus for simultaneously measuring temperature and CO, $CO_2$, and HC gas content of vehicle exhaust comprising:

means for projecting infrared electromagnetic radiation through a plume of vehicle exhaust;

means for receiving the infrared electromagnetic radiation which has passed through the plume of vehicle exhaust and for detecting an intensity of predetermined wavelengths of electromagnetic radiation which are characteristic of absorption spectra of CO, $CO_2$, and HC;

means for receiving infrared electromagnetic radiation emitted by the plume of vehicle exhaust and for detecting intensities of wavelengths of infrared electromagnetic radiation characteristically emitted by CO, $CO_2$, and HC present in the plume of vehicle exhaust at a predetermined temperature; and means for computing the temperature, CO, $CO_2$, and HC content of the plume based on the detected intensities.

13. The invention of claim 12, wherein said predetermined temperature comprises a temperature corresponding to a hot catalytic converter of the vehicle.

14. A method for measuring a temperature of a vehicle exhaust that contains chemical species of interest, comprising the steps of:

intermittently projecting a beam of IR radiation through a region;

prior to the passage of a vehicle through the region, obtaining a first measurement of an absorption of the beam within the region, during a time that the beam is projected, and obtaining a second measurement of an emission of IR radiation from within the region, during a time that the beam is not projected;

after the passage of a vehicle through the region, obtaining a third measurement, during a time that the beam is projected, of an absorption of the beam within the vehicle's exhaust by at least one chemical species of interest, and obtaining a fourth measurement, during a time that the beam is not projected, of an emission of IR radiation from within the vehicle's exhaust by the least one chemical species of interest;

determining a concentration of the at least one chemical species of interest in accordance with the first and third measurements; and determining a temperature of the vehicle's exhaust in accordance with the determined concentration and in accordance with the second and fourth measurements.

15. A system for measuring a temperature of a vehicle exhaust that contains chemical species of interest, comprising:

means for intermittently projecting a beam of IR radiation through a region;

a plurality of spectrally selective IR radiation detection components disposed in a path of said beam; and measurement means having inputs coupled to outputs of said plurality of spectrally selective IR radiation detection components, said measurement means being response to a time prior to a passage of a vehicle through the region for obtaining a first measurement of an absorption of the beam within the region, during a time that the beam is projected, and for obtaining a second measurement of an emission of IR radiation from within the region, during a time that the beam is not projected, said measurement means being further responsive to a time after the passage of the vehicle through the region for obtaining a third measurement, during a time that the beam is projected, of an absorption of the beam within the vehicle's exhaust by at least one chemical species of interest, and for obtaining a fourth measurement, during a time that the beam is not projected, of an emission of IR radiation from within the vehicle's exhaust by the least one chemical species of interest; wherein said measurement means includes means for determining a concentration of the at least one chemical species of interest in accordance with the first and third measurements and for determining a temperature of the vehicle's exhaust in accordance with the determined concentration and in accordance with the second and fourth measurements.

* * * * *